United States Patent [19]

Girgis et al.

[11] Patent Number: 5,364,997
[45] Date of Patent: Nov. 15, 1994

[54] PROCESS FOR CONVERTING MULTI-BRANCHED HEAVY HYDROCARBONS TO HIGH OCTANE GASOLINE

[75] Inventors: Michael J. Girgis, Lawrenceville, N.J.; Ying-Yen P. Tsao, Lahaska, Pa.

[73] Assignee: Mobil Oil Corporation, Fairfax, Va.

[21] Appl. No.: 87,955

[22] Filed: Jul. 6, 1993

Related U.S. Application Data

[63] Continuation-in-part of Ser. No. 955,774, Oct. 5, 1992, Pat. No. 5,284,985.

[51] Int. Cl.$^5$ ................................. C07C 5/27
[52] U.S. Cl. ............................. 585/253; 585/254; 585/313; 585/323; 585/739
[58] Field of Search ............. 585/253, 739, 312, 313, 585/254, 323; 208/111

[56] References Cited

U.S. PATENT DOCUMENTS

| | | | |
|---|---|---|---|
| Re. 28,341 | 2/1975 | Wadlinger et al. | 208/120 |
| 3,130,007 | 4/1964 | Breck | 23/113 |
| 3,216,789 | 11/1965 | Breck et al. | 23/113 |
| 3,293,192 | 12/1966 | Maher et al. | 252/430 |
| 3,308,069 | 3/1967 | Wadlinger et al. | 252/455 |
| 3,354,077 | 11/1967 | Hansford | 208/111 |
| 3,375,065 | 3/1968 | McDaniel et al. | 23/112 |
| 3,402,996 | 9/1968 | Maher et al. | 23/112 |
| 3,449,070 | 6/1969 | McDaniel et al. | 23/113 |
| 3,595,611 | 7/1971 | McDaniel et al. | 23/111 |
| 3,923,639 | 12/1975 | Ciric | 208/111 |
| 3,950,496 | 4/1976 | Ciric | 423/328 |
| 3,972,983 | 8/1976 | Ciric | 423/328 |
| 4,440,871 | 4/1984 | Lok et al. | 502/214 |
| 4,518,485 | 5/1985 | LaPierre et al. | 208/89 |
| 4,554,065 | 11/1985 | Albinson et al. | 208/59 |
| 4,665,273 | 5/1987 | Johnson et al. | 585/739 |
| 4,778,944 | 10/1988 | Zarchy | 585/739 |
| 4,851,109 | 7/1989 | Chen et al. | 208/58 |
| 4,898,722 | 2/1990 | Derouane et al. | 423/328 |
| 5,013,422 | 5/1991 | Absil et al. | 208/27 |
| 5,095,169 | 3/1992 | Skeels et al. | 585/739 |
| 5,235,120 | 8/1993 | Bogdan et al. | 585/253 |
| 5,284,985 | 2/1994 | Girgis et al. | 585/310 |

FOREIGN PATENT DOCUMENTS 1210335 10/1970 United Kingdom.

OTHER PUBLICATIONS

Hutson, T. et al., "Phillips HF Alkylation Process for Alkylation of $C_3$, $C_4$, and $C_5$ Olefins," Handbook Of Petroleum Refining Processes, 1-23 to 1-28 (1986).

Cusher, N., "UCC Total Isomerization Process (TIP)", Handbook Of Petroleum Refining Processes, 5-3 to 5-24 (1986).

Albright, L. et al., "Alkylation of Isobutane with $C_4$ Olefins. 1.First-Step Reactions Using Sulfuric Acid Catalyst," IND.ENG.CHEM.RES., 27, 381-386 (1988).

Maxwell, I. E., "Zeolite Catalysis in Hydroprocessing Technology," Catalysis Today, 1, 385-413 (1987).

Primary Examiner—Anthony McFarlane
Attorney, Agent, or Firm—Alexander J. McKillop; Dennis P. Santini; Lori F. Cuomo

[57] ABSTRACT

The present invention relates to a process for upgrading multi-branched $C_9+$ olefinic and/or paraffinic by-products of heavy hydrocarbon upgrading processes including alkylation, polymerization, and MOGD, to high octane gasoline. Feeds rich in multi-branched $C_9+$ olefins and/or paraffins are contacted with hydrogen at a pressure in the range of about 200 psig to about 2000 psig in the presence of an unsulfided catalyst composition comprising a low acidity molecular sieve having an Alpha Value of 5 or less. Because of the capability of the catalyst to crack at unsubstituted carbon-carbon bonds, the paraffinic products are more highly branched, and thus higher in octane number than those obtained from conventional dual function hydrocracking catalysts having Alpha Values greater than 5.

19 Claims, No Drawings

PROCESS FOR CONVERTING MULTI-BRANCHED HEAVY HYDROCARBONS TO HIGH OCTANE GASOLINE

CROSS REFERENCE TO RELATED APPLICATIONS

This application is a continuation in part of U.S. application Ser. No. 07/955,774 filed Oct. 5, 1992, now U.S. Pat. No. 5,284,985 which is incorporated by reference in its entirety.

FIELD OF THE INVENTION

This application relates to a process for upgrading a multi-branched heavy hydrocarbon feedstream to high octane gasoline using an unsulfided catalyst composition comprising a low acidity molecular sieve.

BACKGROUND OF THE INVENTION

Because of environmental concerns there is a need to include non-aromatic, non-olefinic high octane components such as isoparaffins in the reformulated gasoline pool.

Although some multi-branched $C_{9+}$ olefins may be high octane components, there are restrictions in including olefins in reformulated gasolines. Gasolines having higher olefin contents have been shown to produce increased levels of air toxics and ozone-forming species. Olefins also contribute to fuel system deposits which may increase exhaust emissions. There are also relatively large differences between RON and MON values for olefins, i.e. octane sensitivity. For example, 4-methyl-1-pentene has an RON of 95.7 and an MON of 80.9.

Multi-branched $C_{9+}$ paraffins produced, for example, as a by-product of isobutane alkylation, are also problematic as they fail to meet gasoline boiling point specification.

Therefore, it is an object of the present invention to provide a process for upgrading lower value, undesirable by-product multi-branched $C_{9+}$ olefinic and paraffinic streams to give highly valuable, high octane isoparaffins. It is a further object to improve the economics of olefin upgrading processes by upgrading the less valuable multi-branched $C_{9+}$ olefins produced as by-products to high octane gasoline. A further object of the present invention is to improve the economics of alkylation by upgrading less valuable multi-branched $C_{9+}$ paraffins produced as by-products to high octane gasoline.

SUMMARY OF THE INVENTION

We have now devised a process for producing high octane gasoline rich in naphtha range isoparaffins, generally greater than about 80 wt %, but low in aromatics and olefins, generally less than about 1 wt %. The high octane gasoline product is obtained by contacting a feedstream comprising multi-branched $C_{9+}$ olefins and/or paraffins with hydrogen and an unsulfided catalyst composition comprising a low acidity molecular sieve. The multi-branched $C_{9+}$ olefins and paraffins generally have at least 4 alkyl substituents and preferably at least 6 alkyl substituents. The unsulfided catalyst composition saturates the olefins in the feed and then selectively cracks the resulting multi-branched paraffins as well as any multi-branched paraffins present in the feed to naphtha range multi-branched paraffins having a boiling range of about $C_5$ to 400° C., such as 2,2,4 trimethylpentane. The resulting paraffins are more branched and higher in octane number than those obtained by dual-function hydrocracking catalysts having an Alpha Value greater than 5, resulting in higher octane products. The product comprising high octane naphtha range isoparaffins generally has an RON greater than about 85 and preferably greater than about 90.

Conventional dual-function hydrocracking catalysts catalyze via a different route than the process of the present invention. Paraffin conversion using conventional dual-function hydrocracking catalysts, such as NiW, Pd, or Pt as the metal component, with USY, proceeds via an acid catalyzed carbenium ion mechanism. Cracking by this mechanism occurs preferentially at the carbon bonds having at least one carbon atom with an alkyl substituent resulting in products which are less branched than the reactant. The products are generally normal and mono-branched paraffins which are low in octane number.

The unsulfided catalyst composition of the present invention cracks the unsubstituted carbon-carbon bonds preferentially as compared to conventional dual function hydrocracking catalysts which crack the carbon-carbon bonds having an alkyl substituent preferentially. In addition yields of low end cracking products, such as methane, ethane and propane are minimized using the unsulfided catalyst composition of this invention.

The invention therefore includes a process for producing high octane naphtha range isoparaffins from a heavy hydrocarbon feed comprising a substantial proportion of multi-branched $C_{9+}$ olefins and/or paraffins which comprises contacting said heavy hydrocarbon feed under hydrocracking conditions in the presence of an unsulfided catalyst composition comprising a noble metal and a low acidity molecular sieve having an Alpha Value of 5 or less to saturate said heavy olefins to high molecular weight multi-branched paraffins and cracking said high molecular weight multi-branched paraffins and/or said multi-branched $C_{9+}$ paraffins to produce a product comprising high octane naphtha range isoparaffins.

DETAILED DESCRIPTION OF THE INVENTION

According to the present invention, hydrocarbon feed rich in heavy olefins and/or paraffins is subjected to a selective hydrocracking process. The hydrocracking is carried out over an unsulfided noble metal-containing molecular sieve catalyst of low acidity. The unsulfided catalyst may be a platinum-containing low acidity zeolite.

The feed to the process comprises feeds rich in multi-branched $C_{9+}$ olefins, generally at least about 40 wt %, preferably at least about 60 wt % and more preferably at least about 80 wt %. Feeds rich in multi-branched $C_{12+}$ olefins are preferred. Suitable feeds include by-products of high-olefin upgrading processes, such as Mobil olefins to gasoline/distillate (MOGD) and polymerization. Feeds comprising multi-branched $C_9$ to $C_{16}$ olefins are preferred feeds. Heavy olefin streams formed as a by-product of light olefin upgrading processes, such as catalytic oligomerization and MOGD provide a suitable feedstock for the process of the present invention because of their low sulfur content.

Heavy multi-branched paraffin streams formed as a by-product of alkylation also provide a suitable feedstream for the process of the present invention. Highly paraffinic streams generally comprise at least 80 wt. % C$_9$+ multi-branched paraffins. Any combination of refinery by-product streams comprising a substantial proportion of multi-branched C$_9$+ olefins and/or paraffins may be used in the process of the present invention.

The process operates with a low sulfur feed having less than about 500 ppm sulfur and less than about 50 ppm nitrogen. It is preferable that the feed to the process have less than about 50 ppm sulfur. Feeds having less than about 500 ppm sulfur without preliminary hydrotreatment prior to contacting with the unsulfided catalyst composition of the present invention are preferred.

A preliminary hydrotreating step may be carried out using a conventional hydrotreating catalyst to remove nitrogen and sulfur and to saturate aromatics to naphthenes without substantial boiling range conversion. However, hydrotreating converts olefins to paraffins. Hydrotreating will usually improve catalyst performance and permit lower temperatures, higher space velocities, lower pressures or combinations of these conditions to be employed. Suitable hydrotreating catalysts generally comprise a metal hydrogenation component, usually a Group VIA or VIIIA metal.

The objective of the process of the present invention is to saturate the heavy olefins in the feed to high molecular weight multi-branched paraffins and effect a selective hydrocracking of the high molecular weight multi-branched paraffins as well as any multi-branched heavy paraffins present in the feed to naphtha range isoparaffins. The high molecular weight multi-branched paraffins generally have at least 4 alkyl substituents and preferably at least 6 alkyl substituents.

The process of the present invention operates at a pressure in the range of about 200 to about 2000 psig and preferably in the range of about 800 to about 1200 psig. Generally, the temperature will be in the range of about 270 to about 320° C. and the space velocity will be in the range of 0.4–2.0 LHSV, hr$^{-1}$.

The catalyst used in the process of the present invention is one which has the capability to saturate heavy multi-branched olefins and a high selectivity for cracking the resulting high molecular weight multi-branched paraffins as well as any heavy multi-branched paraffins present in the feed at the bonds connecting unsubstituted carbon atoms. It is the cracking at these bonds that produces highly branched, higher octane products as opposed to cracking at the branched bonds, as with conventional dual function hydrocracking catalysts.

Catalysts with this high selectivity for cracking the bonds connecting unsubstituted carbon atoms are unsulfided and possess a very low molecular sieve, e.g., zeolite acidity. In general terms an Alpha Value of 5 or less should be employed, with preferred Alpha Values of 3 or less.

The noble metals useful in the hydrocracking catalyst include platinum, palladium, and other Group VIIIA metals such as iridium and rhodium, with platinum preferred.

The noble metal may be incorporated into the catalyst by any suitable method such as impregnation or exchange onto the zeolite. The noble metal may be incorporated in the form of a cationic, anionic or neutral complex such as Pt(NH$_3$)$_4$$^{2+}$ and cationic complexes of this type will be found convenient for exchanging metals onto the molecular sieve. The amount of noble metal is suitably from about 0.01 to about 10 percent by weight, normally from about 0.1 to about 2.0 percent by weight. In a preferred method of synthesizing Pt/boron-containing zeolite Beta the platinum compound is tetraamineplatinum hydroxide. The noble metal is preferably introduced into the catalyst composition with a pH neutral solution.

A high level of noble metal dispersion is preferred. For example, platinum dispersion is measured by the hydrogen chemisorption technique and is expressed in terms of H/Pt ratio. The higher the H/Pt ratio, the higher the platinum dispersion. Preferably the resulting molecular sieve should have an H/Pt ratio greater than about 0.8.

Molecular sieves for use as catalyst components herein include zeolites and silicoaluminophosphates. Representative of the zeolites which are useful in the present catalyst are large-pore zeolites including zeolite L, zeolite Y, low sodium ultrastable zeolite Y (USY), zeolite Beta, ZSM-4, ZSM-18, ZSM-20 and mordenite. As used herein, large pore size refers to pores having an average cross section of greater than about 6 Angstroms.

Zeolite Beta is the particularly preferred zeolite for use in the process. Zeolite Beta is described in U.S. Pat. Nos. 3,308,069 and U.S. Pat. Re No. 28,341, incorporated herein by reference.

Zeolite L is described in U.S. Pat. No. 3,216,789, incorporated herein by reference.

Zeolite Y is described in U.S. Pat. No. 3,130,007, incorporated herein by reference.

Low sodium ultrastable zeolite Y (USY) is described in U.S. Pat. Nos. 3,293,192; 3,354,077; 3,375,065; 3,402,996; 3,449,070; and 3,595,611, incorporated herein by reference.

ZSM-4 is described in U.S. Pat. No. 3,923,639, incorporated herein by reference.

ZSM-18 is described in U.S. Pat. 3,950,496, incorporated herein by reference.

Zeolite ZSM-20 is described in U.S. Pat. No. 3,972,983, incorporated herein by reference. Also included within the definition of molecular sieves are crystalline porous silicoaluminophosphates such as those disclosed in U.S. Pat. No. 4,440,871, the catalytic behavior of which is similar to that of the aluminosilicate zeolites. SAPO-37 is described in U.S. Pat. 4,898,722, incorporated herein by reference.

The desired low acidity molecular sieves may be prepared by direct synthesis or converted into the desired low acidity form by various techniques, such as steaming, cation exchange, calcination, and acid treatment.

Preferably, the molecular sieve is composited with a binder. The preferred binder is silica but other silica-containing binders may also be used, for example, silica-alumina, silica-boria, silica-magnesia, silica-zirconia, silica-thoria, silica-berylia, silica-titania as well as ternary compositions such as silica-alumina-boria, silica-alumina-thoria, silica-alumina-zirconia, silica-alumina-magnesia or silica-magnesia-zirconia. The ratio of binder to molecular sieve will typically vary from about 9:1 to about 1:9, more commonly from about 3:1 to about 1:3 (by weight).

The preferred unsulfided catalysts useful in the process of the present invention are steamed Pt/USY, steamed Pt/boron-containing zeolite Beta, acid extracted Pt/USY and acid extracted Pt/boron-containing zeolite Beta.

The process of the present invention is especially useful for upgrading multi-branched $C_{9+}$ paraffinic by-products of alkylation. The process of the present invention may be integrated with a conventional alkylation unit.

The following examples illustrate the process of the present invention.

EXAMPLE 1

A heavy hydrocarbon feedstream containing greater than about 40 wt % multi-branched $C_{9+}$ olefins, such as 4,6,8-trimethyl-1-nonene, is contacted with an unsulfided catalyst comprising Pt on boron-containing zeolite Beta at 300° C., 800 psig and 0.5 LHSV. The multi-branched $C_{9+}$ olefins are hydrogenated and subsequently cracked at the unsubstituted carbon-carbon bonds to yield multi-branched gasoline boiling range paraffins, such as isopentane (RON=92.3), 2,3-dimethylbutane (RON=100.3), 2,2,3-trimethylbutane (RON=101.8) and trimethylpentanes (RON of at least 100). The multi-branched gasoline boiling range paraffins have high octane numbers and being non-olefinic and non-aromatic, are ideal clean gasoline components. The multi-branched gasoline range paraffins also have a lower octane sensitivity and are less prone to gum formation than multi-branched $C_{9+}$ olefinic streams.

EXAMPLE 2

A heavy hydrocarbon feedstream containing greater than about 90 wt. % multi-branched $C_{9+}$ paraffins, such as pentamethylheptanes, and derived from the distillation of products from an alkylation unit is contacted with an unsulfided catalyst comprising Pt on boron-containing zeolite Beta at 300° C., 800 psig and 0.5 LHSV. The multi-branched $C_{9+}$ paraffins are cracked at the unsubstituted carbon-carbon bonds to yield multi-branched gasoline boiling range paraffins, such as isopentane (RON=92.3), 2,3-dimethylbutane (RON=100.3), 2,2,3-trimethylbutane (RON=101.8) and trimethylpentanes (RON of at least 100). The multi-branched gasoline boiling range paraffins have high octane numbers and being non-olefinic and non-aromatic, are ideal clean gasoline components.

Changes and modifications in the specifically described embodiments can be carried out without departing from the scope of the invention which is intended to be limited only by the scope of the appended claims.

What is claimed:

1. A process for producing high octane naphtha range isoparaffins from a heavy hydrocarbon feed comprising a substantial proportion of multi-branched $C_{9+}$ olefins and/or paraffins having at least 4 alkyl substituents which comprises contacting said heavy hydrocarbon feed under hydrocracking conditions in the presence of an unsulfided catalyst composition comprising a noble metal and a low acidity molecular sieve having an Alpha Value of 5 or less to saturate said heavy olefins to high molecular weight multi-branched paraffins and cracking said high molecular weight multi-branched paraffins and/or said multi-branched $C_{9+}$ paraffins to produce a product comprising high octane naphtha range isoparaffins.

2. The process of claim 1 wherein said unsulfided catalyst composition comprises platinum.

3. The process of claim 1 wherein said low acidity molecular sieve is a large-pore zeolite.

4. The process of claim 1 wherein said low acidity molecular sieve is selected from the group consisting of those having the structure of zeolite Y, USY, zeolite L, zeolite Beta, ZSM-4, ZSM-18, ZSM-20 and mordenite.

5. The process of claim 1 wherein said unsulfided catalyst composition comprises platinum and a boron-containing zeolite having the structure of zeolite Beta.

6. The process of claim 1 wherein said unsulfided catalyst composition comprises platinum and a zeolite having the structure of USY.

7. The process of claim 1 wherein said low acidity molecular sieve has an Alpha Value of 3 or less.

8. The process of claim 1 wherein said product comprising high octane naphtha range isoparaffins has an RON greater than about 85.

9. The process of claim 1 wherein said hydrocracking conditions include a LHSV in the range of from about 0.4 to about 2.0 $hr^{-1}$.

10. The process of claim 1 wherein said hydrocracking conditions include a temperature in the range of from about 270° to about 320° C.

11. The process of claim 1 wherein said hydrocracking conditions include a pressure in the range of about 200 to about 2000 psig.

12. The process of claim 1 wherein said multi-branched $C_{9+}$ olefins and/or paraffins have at least 6 alkyl substituents.

13. The process of claim 1 wherein said heavy hydrocarbon feed comprises at least 40 wt % multi-branched $C_{9+}$ olefins.

14. The process of claim 1 wherein said heavy hydrocarbon feed comprises at least 80 wt % multi-branched $C_{9+}$ paraffins.

15. The process of claim 14 wherein said product comprising high octane naphtha range isoparaffins has an RON greater than about 90.

16. The process of claim 1 wherein said heavy hydrocarbon feed comprises multi-branched $C_{12+}$ olefins.

17. The process of claim 1 wherein said heavy hydrocarbon feed is a by-product from an alkylation process.

18. The process of claim 1 wherein said heavy hydrocarbon feed is a by-product of an olefin upgrading process.

19. The process of claim 1 wherein said contacting under hydrocracking conditions is conducted without a preliminary hydrotreatment step.

\* \* \* \* \*